United States Patent
Zimmerling et al.

(10) Patent No.: US 9,008,792 B2
(45) Date of Patent: Apr. 14, 2015

(54) MRI-SAFE IMPLANT ELECTRONICS

(75) Inventors: Martin Zimmerling, Patsch (AT); Josef Baumgartner, Ranggen (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 1172 days.

(21) Appl. No.: 12/857,848

(22) Filed: Aug. 17, 2010

(65) Prior Publication Data

US 2011/0043210 A1 Feb. 24, 2011

Related U.S. Application Data

(60) Provisional application No. 61/235,386, filed on Aug. 20, 2009.

(51) Int. Cl.

| | | |
|---|---|---|
| *A61N 1/08* | (2006.01) | |
| *G01R 33/28* | (2006.01) | |
| *A61B 5/00* | (2006.01) | |
| *A61N 1/378* | (2006.01) | |
| *A61N 1/37* | (2006.01) | |
| *H02J 7/02* | (2006.01) | |

(52) U.S. Cl.
CPC ............ *G01R 33/285* (2013.01); *A61B 5/0031* (2013.01); *A61N 1/3718* (2013.01); *A61N 1/378* (2013.01); *G01R 33/288* (2013.01); *H02J 7/025* (2013.01); *H04R 2225/49* (2013.01); *H04R 2225/67* (2013.01)

(58) Field of Classification Search
CPC ... A61N 1/0541; A61N 1/08; A61N 1/36032; A61N 1/372; A61N 1/37211; A61N 1/37217; A61N 1/37223; A61N 1/378; A61N 1/3787

USPC ............................................. 607/33, 61, 63
See application file for complete search history.

(56) References Cited

U.S. PATENT DOCUMENTS

| | | | |
|---|---|---|---|
| 5,630,835 A | 5/1997 | Brownlee | 607/60 |
| 6,292,678 B1 | 9/2001 | Hall et al. | 600/374 |
| 6,348,070 B1 | 2/2002 | Teissl et al. | 623/11.11 |
| 6,747,452 B1* | 6/2004 | Jectic et al. | 324/311 |
| 6,838,963 B2 | 1/2005 | Zimmerling et al. | 335/205 |
| 6,850,067 B1* | 2/2005 | Burl et al. | 324/322 |
| 7,091,806 B2 | 8/2006 | Zimmerling et al. | 335/207 |

(Continued)

FOREIGN PATENT DOCUMENTS

| | | |
|---|---|---|
| WO | WO 03/092326 | 11/2003 |
| WO | WO 2008/132653 | 11/2008 |
| WO | WO 2009/029977 | 3/2009 |

OTHER PUBLICATIONS

Teissl, et al, "Cochlear Implants: In Vitro Investigation of Electromagnetic Interference at MR Imaging—compatibility and Safety Aspects", *Radiology Radiol. Soc. North America USA*, vol. 208, No. 3, Sep. 1998, pp. 700-708, XP009140916, ISSN: 0033-8419, pp. 700-701.

(Continued)

*Primary Examiner* — Allen Porter, Jr.
(74) *Attorney, Agent, or Firm* — Sunstein Kann Murphy & Timbers LLP

(57) ABSTRACT

A power supply arrangement for an implantable electronic system is described. An MRI power supply arrangement cooperates with an implantable power supply circuit to provide a high output impedance for implanted circuitry during magnetic resonance imaging (MRI).

4 Claims, 2 Drawing Sheets

(56) References Cited

U.S. PATENT DOCUMENTS

| | | | |
|---|---|---|---|
| 7,190,247 | B2 | 3/2007 | Zimmerling .................. 335/205 |
| 7,566,296 | B2 | 7/2009 | Zimmerling et al. ........... 600/25 |
| 7,609,061 | B2 | 10/2009 | Hochmair ..................... 324/307 |
| 7,642,887 | B2 | 1/2010 | Zimmerling .................. 335/296 |
| 8,489,199 | B2* | 7/2013 | Rofougaran ................... 607/60 |
| 8,515,533 | B2* | 8/2013 | Rofougaran et al. ............. 607/2 |
| 2001/0035754 | A1* | 11/2001 | Sato ............................. 324/318 |
| 2003/0176906 | A1* | 9/2003 | Lee .............................. 607/116 |
| 2005/0030032 | A1* | 2/2005 | Kwok et al. ................. 324/318 |
| 2006/0133733 | A1* | 6/2006 | Koste et al. .................... 385/48 |
| 2007/0167867 | A1 | 7/2007 | Wolf ............................ 600/561 |
| 2007/0191914 | A1* | 8/2007 | Stessman ....................... 607/63 |
| 2008/0129435 | A1 | 6/2008 | Gray ............................ 336/184 |
| 2008/0161886 | A1* | 7/2008 | Stevenson et al. .............. 607/60 |
| 2009/0204171 | A1* | 8/2009 | Ameri ............................ 607/36 |
| 2009/0219025 | A1* | 9/2009 | Fujimoto ...................... 324/322 |
| 2010/0023095 | A1* | 1/2010 | Stevenson et al. .............. 607/63 |
| 2010/0166279 | A1* | 7/2010 | Seifert et al. .................. 382/131 |

OTHER PUBLICATIONS

Teissl, et al, "Magnetic Resonance Imaging and Cochlear Implants: Compatibility and Safety Aspects", *Journal of Magnetic Resonance Imaging*, 9:26-38 (1999), XP-002503038.

European Patent Office; Officer Jorg Skalla, International Search Report and Written Opinion, PCT/US2010/045699, dated Nov. 10, 2010.

* cited by examiner

MRI-SAFE IMPLANT ELECTRONICS

This application claims priority from U.S. Provisional Patent Application 61/235,386, filed Aug. 20, 2009, which is incorporated herein by reference.

FIELD OF THE INVENTION

The present invention relates to implantable medical devices, specifically, increasing the safety of such devices for use with Magnetic Resonance Imaging (MRI).

BACKGROUND ART

The widely used technique of Magnetic Resonance Imaging (MRI) can pose various risks for patients with implantable electronic devices such as cochlear implant systems, both to the patient and/or to the implant. For example, in implants with elongated electrodes, interactions with the induced RF pulses and switching gradient fields can lead to MRI-induced heating at electrode contacts which can be especially dangerous with longer implant electrodes such as in cardiac pacemakers, spinal cord stimulators, and deep brain stimulators. With cochlear implants, this potential risk may be somewhat lower because of the relatively short electrode. MRI-induced currents also can result in unintentional stimulation of the target neural tissue. At best, this may be just uncomfortable for the patient (e.g. with cochlear implants there can be unintentional auditory sensations during MRI). At worst, such unintentional stimulation may be potentially dangerous (e.g. with deep brain stimulators). The strength of MRI-induced effects depends on multiple factors such as electrode length, electrode contact size, MRI equipment, and MRI sequences used. The impedance, inductance and capacitance of the electrode circuit and the stimulator housing also have a significant influence on the strength of these effects.

The impedance within the electrode circuit is the sum of the electrode impedance, the wiring impedance, and the impedance of the electronic output circuit which typically consists of CMOS switches and transistors. The impedance of such semiconductors is relatively undefined when the implant has no power supply, such as when the external power supply components are removed for safety reasons before performing an MRI. Without a power supply, such semiconductors typically act as a diode to rectify signals picked up by the electrode circuit such as RF signal pulses during MRI. Such spurious signals (the Larmor frequency of a 1.5 Tesla MR scanner is 63.9 MHz) are only limited by the capacitance of the diode, typically on the order of 10 pF.

Currently, MRI-related heating of electrodes and elongated implant structures is avoided by having a prohibition against the use of MRI on patients having such implants. This may be either a complete prohibition against MRI, or a partial limit that permits only low-field MRI and/or low SAR values. Alternatively or in addition, electrode wire coiling may be used to improve safety with MRI.

SUMMARY OF THE INVENTION

Embodiments of the present invention are directed to a power supply arrangement for an implantable electronic system such as a cochlear implant system. An MRI power supply arrangement cooperates with an implantable power supply circuit to provide a high output impedance for implanted circuitry during magnetic resonance imaging (MRI).

In further specific embodiments, the MRI power supply arrangement may include an implantable MRI power supply circuit coupled to the implantable power supply circuit for providing a power supply voltage to the implanted circuitry during MRI.

In other specific embodiments, the MRI power supply arrangement may include an external MRI power supply circuit coupled to the implantable power supply circuit for providing a power supply voltage to the implanted circuitry during MRI. The external MRI power supply circuit may be battery powered or powered by RF pulses generated during MRI. There may also be a removable external holding magnet for cooperating with a corresponding implant magnet to establish a correct position of the external MRI power supply circuit with respect to the implantable power supply circuit.

DETAILED DESCRIPTION OF SPECIFIC EMBODIMENTS

Embodiments of the present invention are directed to a power supply arrangement for an implantable electronic system such as a cochlear implant system. An MRI power supply arrangement cooperates with an implantable power supply circuit to provide a high output impedance for implanted circuitry during magnetic resonance imaging (MRI). More specifically, the time-invariant magnetic fields that are present during MRI are exploited to generate a sufficient power supply for the implanted electronic circuits so that the semiconductor outputs are in a well-defined high-impedance state during the MRI. This results in an implantable system with improved MRI-safety with regard to RF-induced electrode heating and currents.

Many Active Implantable Medical Devices (AIMD's) are partially or fully implantable, and they include an implantable coil for transferring an electrical signal through the skin that provides power to one or more implanted electronic circuits (and which also typically includes a data component that is not relevant in the present discussion).

Figure 1:
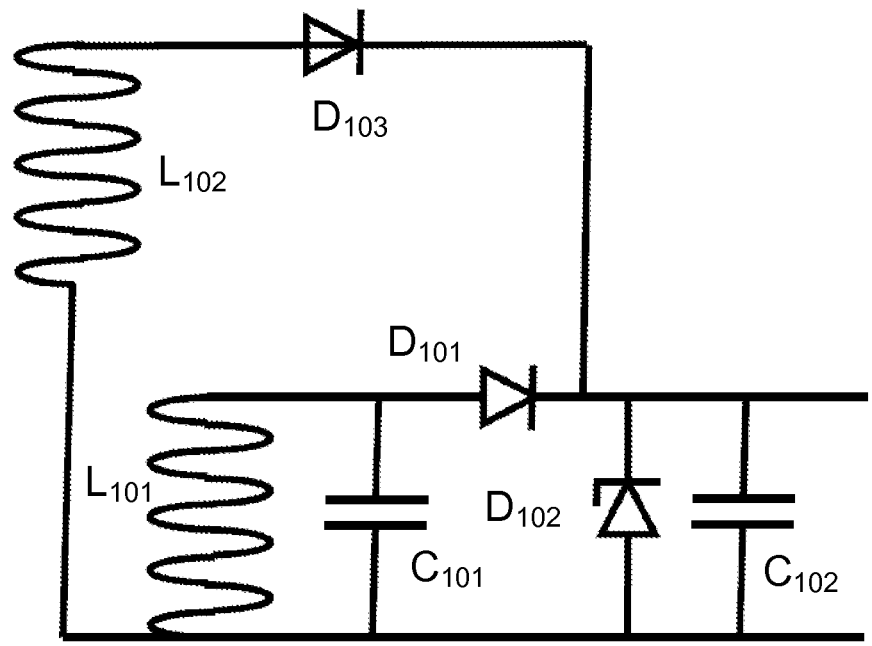
FIG. 1 shows components of an implantable MRI power supply circuit according to one embodiment which is coupled to the implantable power supply circuit for providing a power supply voltage to the implanted circuitry during MRI.

FIG. 1 shows one approach based on an implantable MRI power supply arrangement that is coupled to the main implant power supply circuit which does not need an external coil to provide power to the implant during MRI. Normally, an externally generated RF electrical signal is received by implant receiver coil $L_{101}$, which forms a resonant circuit with parallel capacitor $C_{101}$. Schottky diode $D_{101}$ rectifies the RF signal present in the $L_{101}/C_{101}$ resonant circuit to develop the main implant supply voltage, which is filtered by output capacitor $C_{102}$. Zener diode $D_{102}$ provides over-voltage protection. To this main power supply circuit is added a new implantable MRI power supply circuit in which MRI inductance $L_{102}$ has broad-band inductive coupling characteristics to sense the RF pulses from a wide range of MR scanner fields. MRI rectifier diode $D_{103}$ develops the received pulses to generate an implant supply voltage during MRI which is sufficiently high to power the semiconductor outputs of the implant circuits into a well-defined high-impedance state during the MRI.

Figure 2:
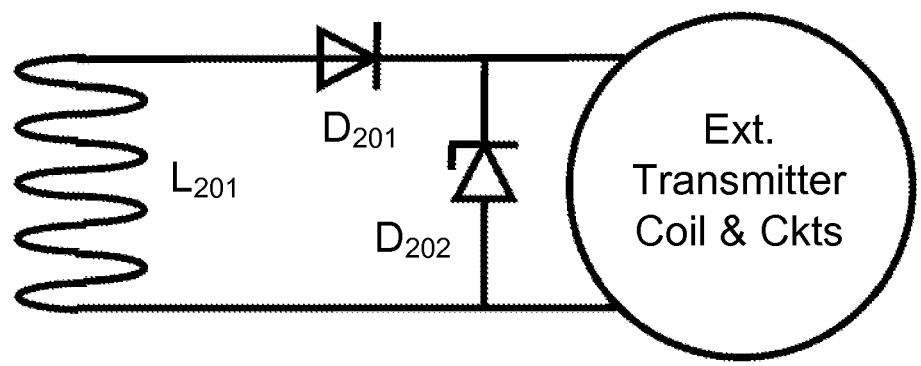
FIG. 2 shows an embodiment of an external MRI power supply circuit which is powered by RF pulses generated during MRI.

While embodiments based on an implantable MRI power supply circuit are useful for new implant systems, there are a large number of existing implant systems which are already in use without such a protective circuit built in. For such existing systems, an external MRI power supply is useful. FIG. 2 shows one embodiment of an external MRI power supply circuit for use during MRI which is placed onto the skin over the implant circuit which converts the energy of the RF pulses into a signal which is transferred through the skin and which is suited to generate a sufficiently high supply voltage within the implant. The arrangement is powered by RF pulses generated during MRI: MRI inductance $L_{201}$ senses RF pulses from the MRI scanner field, and MRI diode $D_{201}$ rectifies the pulses to generate an external electrical signal for inductive transmission through the skin by the external transmitter circuits to the implanted receiver coil. Zener diode $D_{202}$ provides over voltage protection. This MRI signal is developed by the implanted circuits to generate an implant supply voltage during the MRI which is sufficiently high to power the semiconductor outputs of the implant circuits into a well-defined high-impedance state during the MRI.

Figure 3:
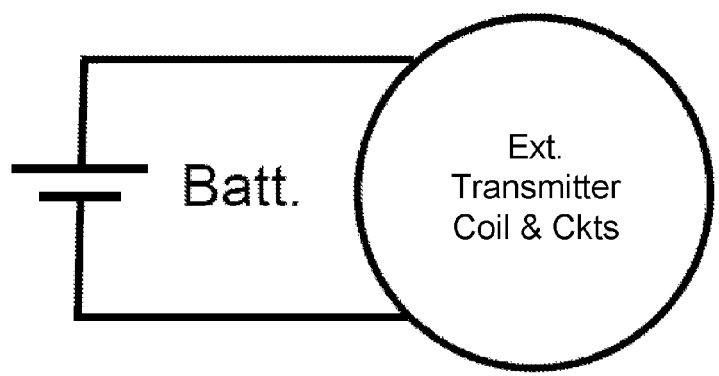
FIG. 3 shows an embodiment of an external MRI power supply circuit which is battery powered.

FIG. 3 shows an embodiment of another external MRI power supply circuit for use during MRI which is battery powered and which contains an external coil that is placed on the skin over the implant circuit. The external battery powered coil generates a signal which is transferred through the skin and is suitable to generate a sufficiently high supply voltage within the implant to power the semiconductor outputs of the implant circuits into a well-defined high-impedance state during the MRI.

Figure 4:
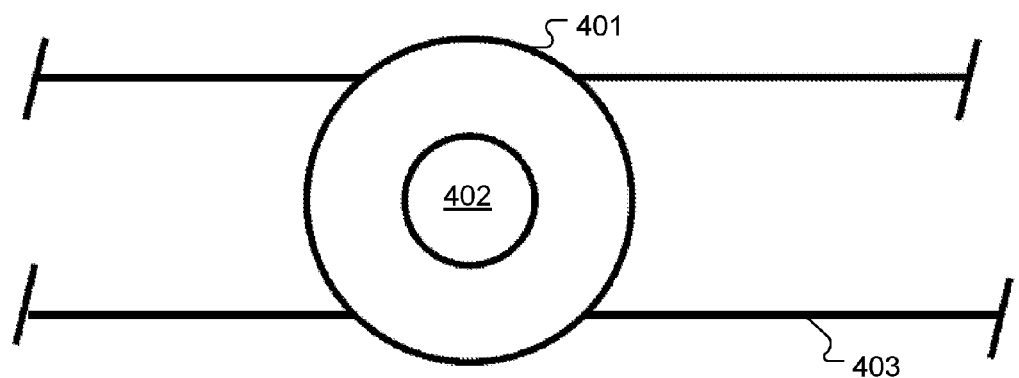
FIG. 4 shows an embodiment of an external MRI power supply having a removable magnet and a headband.

FIG. 4 shows an embodiment of an external MRI transmitting coil 401 as in FIG. 2 or FIG. 3 for use during MRI which also includes a removable external holding magnet 402 and a headband 403. Prior to MRI, such an external transmitting coil 401 with the removable external holding magnet 402 attached would be placed over the implanted receiver coil to cooperate with a corresponding implant magnet to establish a correct position of the external MRI transmitting coil 401 with respect to the implantable power supply circuit. The head band 403 is then attached around the head to fix the external MRI transmitting coil 401 in the correct position, after which, the removable external holding magnet 402 can be removed, and the MRI can be performed.

The MRI electrical power signal that is inductively transferred to the implant for MRI supply voltage can be generated in any of several different ways. For example, specific embodiments could be based on use of a frequency converter (e.g. frequency divider or frequency multiplier). Alternatively or in addition, an external broadband receiver can be used to convert the MRI RF signal into a DC voltage (e.g. by rectifying and low-pass filtering) which can be used to drive an oscillator running at the frequency of the inductive link.

Although various exemplary embodiments of the invention have been disclosed, it should be apparent to those skilled in the art that various changes and modifications can be made which will achieve some of the advantages of the invention without departing from the true scope of the invention.

What is claimed is:

1. A power supply arrangement for an implantable electronic system comprising:
a main implant power supply comprising:
  i. an implant receiver coil $L_{101}$ and a parallel capacitor $C_{101}$ arranged to form a resonant circuit that receives an externally generated RF signal,
  ii. a Schottky diode $D_{101}$ in series with the $L_{101}/C_{101}$ resonant circuit and configured to rectify the RF signal received by the $L_{101}/C_{101}$ resonant circuit, and
  iii. a power supply output circuit comprising an output capacitor $C_{102}$ in parallel with an overvoltage Zener diode $D_{102}$, the power supply output circuit being arranged in parallel with the Schottky diode $D_{101}$ and the $L_{101}/C_{101}$ resonant circuit to receive the rectified RF signal from the Schottky diode $D_{101}$ and develop a main implant power supply voltage output during normal operation of the implantable electronic system; and
an implantable magnetic resonance imaging (MRI) power supply arrangement comprising:
  i. an MRI inductance $L_{102}$ configured to have broadband inductive coupling characteristics to sense RF pulses from MR scanner fields during MRI, and
  ii. an MRI rectifier diode $D_{103}$ in series with the MRI inductance $L_{102}$ and arranged to rectify the RF pulses sensed by the MRI inductance $L_{102}$ during MRI;
wherein the MRI power supply arrangement is arranged in parallel with the power supply output circuit and in parallel with the Schottky diode $D_{101}$ and the $L_{101}/C_{101}$ resonant circuit so as to cooperate with the main implant power supply to provide a high impedance state power supply voltage output during MRI.

2. A power supply arrangement according to claim 1, wherein the implanted circuitry is for a cochlear implant system.

3. A method for providing electrical power to an implantable electronic system, the method comprising:
providing a main implant power supply voltage during normal operation of the implantable electronic system from a main implant power supply comprising:
  i. an implant receiver coil $L_{101}$ and a parallel capacitor $C_{101}$ arranged to form a resonant circuit that receives an externally generated RF signal, and
  ii. a Schottky diode $D_{101}$ in series with the $L_{101}/C_{101}$ resonant circuit and configured to rectify the RF signal received by the $L_{101}/C_{101}$ resonant circuit, and
  iii. a power supply output circuit comprising an output capacitor $C_{102}$ in parallel with an overvoltage Zener diode $D_{102}$, the power supply output circuit being arranged in parallel with the Schottky diode $D_{101}$ and the $L_{101}/C_{101}$ resonant circuit to receive the rectified RF signal from the Schottky diode $D_{101}$ and develop a main implant power supply voltage output during normal operation of the implantable electronic system,
providing a high impedance state power supply voltage output during magnetic resonance imaging (MRI) from an implantable MRI power supply arrangement comprising:
  i. an MRI inductance $L_{102}$ configured to have broadband inductive coupling characteristics to sense RF pulses from MR scanner fields during MRI, and
  ii. an MRI rectifier diode $D_{103}$ in series with the MRI inductance $L_{102}$ and arranged to rectify the RF pulses sensed by the MRI inductance $L_{102}$ during MRI, wherein the MRI power supply arrangement is arranged in parallel with the power supply output circuit and in parallel with the Schottky diode $D_{101}$ and the $L_{101}/C_{101}$ resonant circuit so as to cooperate with the main implant power supply to provide the high impedance state power supply voltage output during MRI.

4. A method according to claim 3, wherein the implanted circuitry is for a cochlear implant system.

* * * * *